US00PP15329P2

(12) United States Plant Patent
Fyfe

(10) Patent No.: US PP15,329 P2
(45) Date of Patent: Nov. 16, 2004

(54) ***PITTOSPORUM* PLANT NAMED 'GOLF BALL'**

(50) Latin Name: *Pittosporum tenuifolium*
Varietal Denomination: Golf Ball

(75) Inventor: Mark Nelson Fyfe, Hastings H.B. (NZ)

(73) Assignee: Plant Production Ltd., Napier (NZ)

( * ) Notice: Subject to any disclaimer, the term of this patent is extended or adjusted under 35 U.S.C. 154(b) by 0 days.

(21) Appl. No.: 10/724,993

(22) Filed: Dec. 1, 2003

(51) Int. Cl.[7] ..... A01H 5/00
(52) U.S. Cl. ..... Plt./234
(58) Field of Search ..... Plt./234

*Primary Examiner*—Kent Bell
*Assistant Examiner*—Louanne Krawczewicz Myers
(74) *Attorney, Agent, or Firm*—C. A. Whealy

(57) ABSTRACT

A new and distinct *Pittosporum* plant named 'Golf Ball', characterized by its compact and roughly spherical plant form; vigorous growth habit; freely basal branching habit; dense and bushy plant habit; and dark green-colored leaves.

1 Drawing Sheet

Botanical classification/cultivar designation: *Pittosporum tenuifolium* cultivar Golf Ball.

BACKGROUND OF THE INVENTION

The present invention relates to a new and distinct cultivar of *Pittosporum*, botanically known as *Pittosporum tenuifolium*, and hereinafter referred to by the name 'Golf Ball'.

The new *Pittosporum* is a product of a self-pollination of an unidentified selection of *Pittosporum tenuifolium*, not patented. The new *Pittosporum* was discovered and selected by the Inventor in a controlled environment in Clive, New Zealand on Nov. 20, 1997, as a single plant within the progeny resulting from the self-pollination.

Asexual reproduction of the new *Pittosporum* by cuttings taken in a controlled environment in Napier, New Zealand, since Mar. 28, 1998, has shown that the unique features of this new *Pittosporum* are stable and reproduced true to type in successive generations.

SUMMARY OF THE INVENTION

The cultivar Golf Ball has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Golf Ball'. These characteristics in combination distinguish 'Golf Ball' as a new and distinct cultivar of *Pittosporum:*

1. Compact and roughly spherical plant form.
2. Vigorous growth habit.
3. Freely basal branching habit, dense and bushy plant habit.
4. Dark green-colored leaves.

Plants of the new *Pittosporum* differ from plants of the parent selection primarily in plant form.

Plants of the new *Pittosporum* can be compared to plants of the *Pittosporum* cultivar Little Squirt, not patented. In side-by-side comparisons conducted in Napier, New Zealand, plants of the new *Pittosporum* differed from plants of the cultivar Little Squirt in the following characteristics:

1. Plants of the new *Pittosporum* were more compact and more rounded than plants of the cultivar Little Squirt.
2. Plants of the new *Pittosporum* had shorter internodes and were denser and bushier than plants of the cultivar Little Squirt.
3. Plants of the new *Pittosporum* were more freely basally branching than plants of the cultivar Little Squirt.

BRIEF DESCRIPTION OF THE PHOTOGRAPHS

The accompanying colored photographs illustrate the overall appearance of the new *Pittosporum*, showing the colors as true as it is reasonably possible to obtain in colored reproductions of this type. Colors in the photographs may differ slightly from the color values cited in the detailed botanical description which accurately describe the colors of the new *Pittosporum.*

The photograph at the top of the sheet comprises a side perspective view of a typical plant of 'Golf Ball' grown in a container.

The photograph at the bottom left of the sheet is a close-up view of typical leaves of 'Golf Ball'.

DETAILED BOTANICAL DESCRIPTION

The aforementioned photographs and following observations and measurements describe plants grown in Azusa, Calif., grown in five-gallon containers in an outdoor nursery during the summer and under conditions which closely approximate commercial production. During the production of the plants, day temperatures ranged from 29 to 32° C. and night temperatures ranged from 13 to 16° C. Plants were about 16 months old when the photographs and the description were taken. Plants were pruned to maintain the plant's symmetry. In the description color references are made to The Royal Horticultural Society Colour Chart, 1995 Edition, except where general terms of ordinary dictionary significance are used.

Botanical classification: *Pittosporum tenuifolium* cultivar Golf Ball.

Parentage: Self-pollination of an unidentified selection of *Pittosporum tenuifolium,* not patented.

Propagation:

*Type.*—By cuttings.

*Time to initiate roots, summer.*—About 24 days at 21° C.

*Time to initiate roots, winter.*—About 28 days at 15° C.

*Time to produce a rooted young plant, summer.*—About 220 days at 21° C.

*Time to produce a rooted young plant, winter.*—About 270 days at 12° C.

*Root description.*—Wiry; light brown in color.

*Rooting habit.*—Sparse to moderately dense.

Plant Description:

*Plant type.*—Perennial evergreen shrub.

*Plant form and growth habit.*—Compact and roughly spherical plant form. Moderately vigorous growth habit.

*Branching habit.*—Freely branching; dense and bushy plant habit; usually about eight main branches each with about three lateral branches.

*Plant height.*—About 32 cm.

*Plant diameter* (*area of spread*).—About 39 cm.

*Lateral branch description.*—Length, primary branches: About 28 cm. Length, lateral branches: About 17 cm. Diameter, primary branches: About 6 mm. Diameter, lateral branches: About 2 mm. Internode length: About 5 mm. Aspect: Upright and outwardly. Texture: Smooth, glabrous. Color: 177A to 177B.

*Foliage description.*—Arrangement: Alternate, simple. Length: About 2.6 cm. Width: About 1.5 cm. Shape: Elliptical. Apex: Acute. Base: Obtuse. Margin: Entire. Texture, upper and lower surfaces. Smooth, glabrous. Venation pattern: Pinnate. Color: Developing leaves, upper surface: 146A. Developing leaves, lower surface: 147B. Fully expanded leaves, upper surface: 147A. Fully expanded leaves, lower surface: 147B. Venation, upper surface: 146B. Venation, lower surface: 147C. Petiole: Length: About 6 mm. Diameter: About 1 mm. Texture, upper and lower surfaces: Smooth, glabrous; leathery. Color, upper and lower surfaces: 147C.

Flower description: Flower development has not been observed on plants of the new *Pittosporum*.

Disease/pest resistance: Plants of the new *Pittosporum* have been observed to be relatively resistant to root rot pathogens, such as *Phytophthora*. Plants of the new *Pittosporum* have not been observed to be resistant to other pathogens and pests common to *Pittosporum*.

Garden performance: Plants of the new *Pittosporum* have been observed to have excellent tolerance to wind, rain and temperatures from −6° C. to 43° C.

It is claimed:

1. A new and distinct *Pittosporum* plant named 'Golf Ball', as illustrated and described.

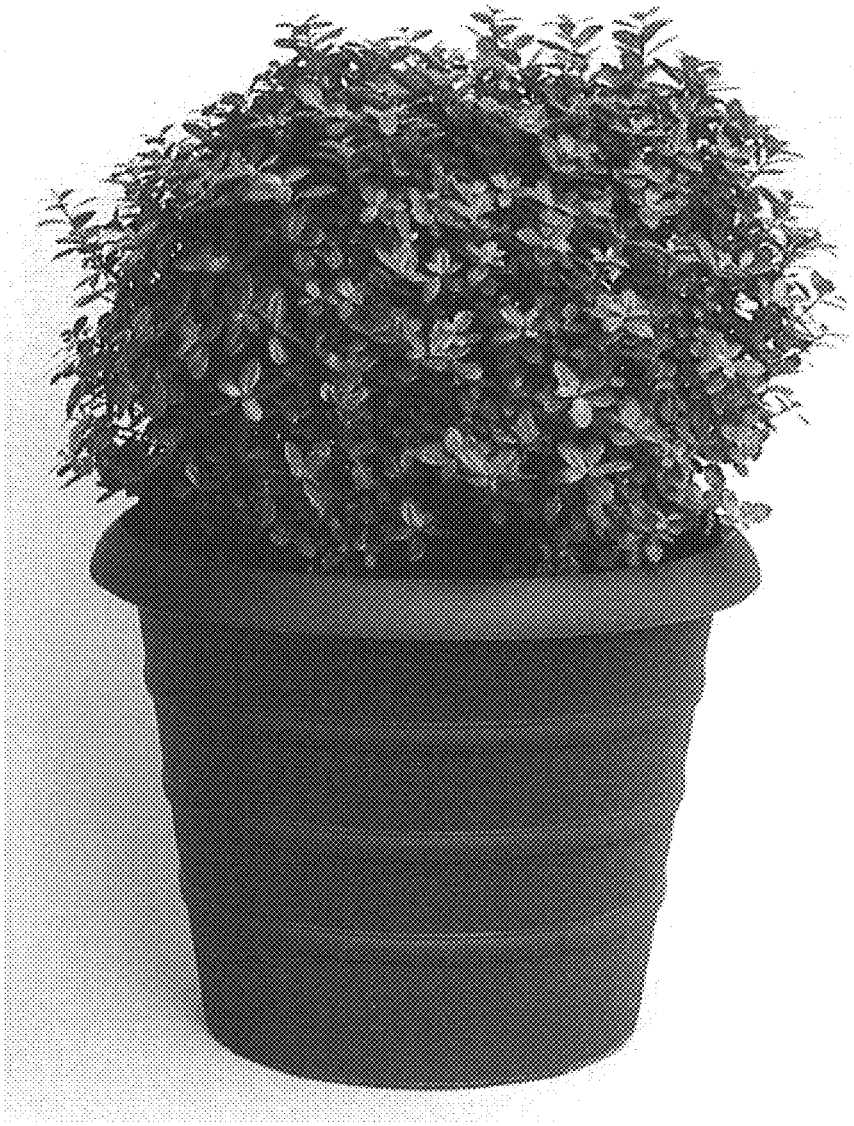
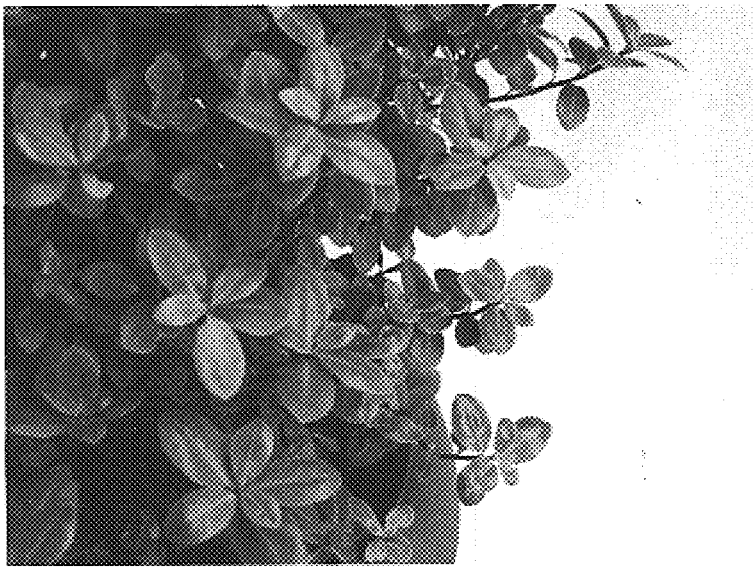

* * * * *